(12) United States Patent
Longstaff

(10) Patent No.: US 7,678,091 B2
(45) Date of Patent: Mar. 16, 2010

(54) COLOSTOMY BAG

(76) Inventor: Charles W. Longstaff, 302-1371 Blackwood Street, White Rock, BC (CA) V4b 3V2

( * ) Notice: Subject to any disclaimer, the term of this patent is extended or adjusted under 35 U.S.C. 154(b) by 0 days.

(21) Appl. No.: 11/724,243

(22) Filed: Mar. 15, 2007

(65) Prior Publication Data

US 2008/0228155 A1 Sep. 18, 2008

(51) Int. Cl.
*A61F 5/44* (2006.01)
(52) U.S. Cl. .................. 604/333; 604/317; 604/323; 604/324; 604/326; 604/327; 604/331; 604/332; 604/337; 604/338; 604/339; 604/341; 604/350; 604/355
(58) Field of Classification Search .............. 604/317, 604/323, 324, 326, 327, 331–333, 337–339, 604/341, 350, 355
See application file for complete search history.

(56) References Cited

U.S. PATENT DOCUMENTS

| | | | |
|---|---|---|---|
| 2,555,086 A * | 5/1951 | Guinn | 604/333 |
| 3,439,677 A * | 4/1969 | Bonfils | 604/333 |
| 3,759,260 A * | 9/1973 | Nolan et al. | 604/333 |
| 3,952,727 A * | 4/1976 | Nolan | 604/333 |
| 4,203,445 A * | 5/1980 | Jessup et al. | 604/333 |
| 4,211,224 A | 7/1980 | Kubach | |
| 4,274,848 A | 6/1981 | La Gro | |
| 4,319,571 A * | 3/1982 | Winchell | 604/342 |
| 4,372,308 A | 2/1983 | Steer | |
| 4,490,145 A * | 12/1984 | Campbell | 604/333 |
| 4,863,447 A | 9/1989 | Smith | |
| 4,911,699 A | 3/1990 | Fenton | |
| 5,348,546 A | 9/1994 | Norton | |
| 5,643,234 A | 7/1997 | Lesko | |
| 5,728,080 A | 3/1998 | Suyama | |
| 6,007,525 A | 12/1999 | Martell | |
| 6,050,983 A | 4/2000 | Moore | |
| 6,135,986 A | 10/2000 | Leisner | |
| 6,695,826 B2 * | 2/2004 | Villefrance | 604/333 |
| 7,090,664 B2 | 8/2006 | Holter | |
| 7,150,728 B2 | 12/2006 | Hansen | |

* cited by examiner

*Primary Examiner*—Tatyana Zalukaeva
*Assistant Examiner*—Ilya Y Treyger
(74) *Attorney, Agent, or Firm*—Andrew Hicks; Hicks & Associates

(57) ABSTRACT

A colostomy bag provided with a stoma ring, a gas outlet and an external deodorizing filter in which a vertical baffle is provided intermediate the stoma ring and the gas outlet and extending from the upper marginal wall of the bag and a level slightly below the lowest point of the stoma ring. The baffle is designed to prevent feces from being squeezed sideways and upwardly into the gas outlet and clogging it.

5 Claims, 5 Drawing Sheets

COLOSTOMY BAG

FIELD OF INVENTION

This invention relates to a colostomy bag and more particularly to a colostomy bag having an external gas filter and deodorizing device.

BACKGROUND OF INVENTION

Colostomy is a surgical procedure to connect a patient's colon to an artificial anus, usually called a stoma, formed in the abdominal wall. Having undergone a colostomy the patient must always keep a colostomy bag in position against the stoma to receive feces and gas discharged through the stoma. An abdominal belt is usually used to hold the bag in position against the stoma immediately behind the normal beltline of a patient's clothing, where the clothing is normally tightest. In addition, the bag is normally provided with a gas vent to prevent gas build up and over inflation of the bag, and in order to eliminate offensive odours caused by the escaping gas it is common practice to provide an exterior deodorizing filter in the gas vent line. Attention is directed to U.S. Pat. No. 6,007,525 issued 18 Dec. 1999 and U.S. Pat. No. 7,090,664 issued 15 Aug. 2006 as illustrative of present colostomy bags. While these bags are generally effective to release the gases in a discreet and odourless manner, there remains the problem that the gas vent tube is placed near the top of the bag and adjacent to the stoma. Feces entering the bag from the stoma are frequently squeezed sideways and upwardly by the pressure of the patient's belt or waistband rather than falling under gravity to the bottom of the bag, with the result that the relatively narrow vent tube becomes plugged and the bag has to be removed prematurely for cleaning. In U.S. Pat. No. 7,090,664 an attempt to overcome this problem has been suggested by the provision of a short horizontal baffle to protect the vent tube from ingress of feces, but this is not entirely satisfactory and does not eliminate the problem.

OBJECT OF INVENTION

It is an object of the present invention to overcome the drawbacks noted above and to provide a colostomy bag having an external gas vent and deodorizing device together with an effective baffle system which will substantially eliminate plugging of the vent tube with feces.

BRIEF STATEMENT OF INVENTION

By one aspect of this invention there is provided a colostomy bag formed by a pair of superimposed planar sheets of a flexible thermoplastic material heat sealed to each other around marginal edges thereof, said bag, when in operational position, including:

(i) a stoma ring so as to provide feces and gas inlet means adjacent an upper marginal edge of said bag;

(ii) gas outlet means adjacent said upper marginal edge and a first side marginal edge of said bag; and (iii) baffle means intermediate between said stoma ring and said gas outlet means and extending vertically between said upper marginal edge of said bag and a position below a lower edge of said stoma ring, so as to divert feces away from said gas outlet means and toward a lower marginal side edge of said bag.

DETAILED DESCRIPTION OF PREFERRED EMBODIMENTS

Figure 1:
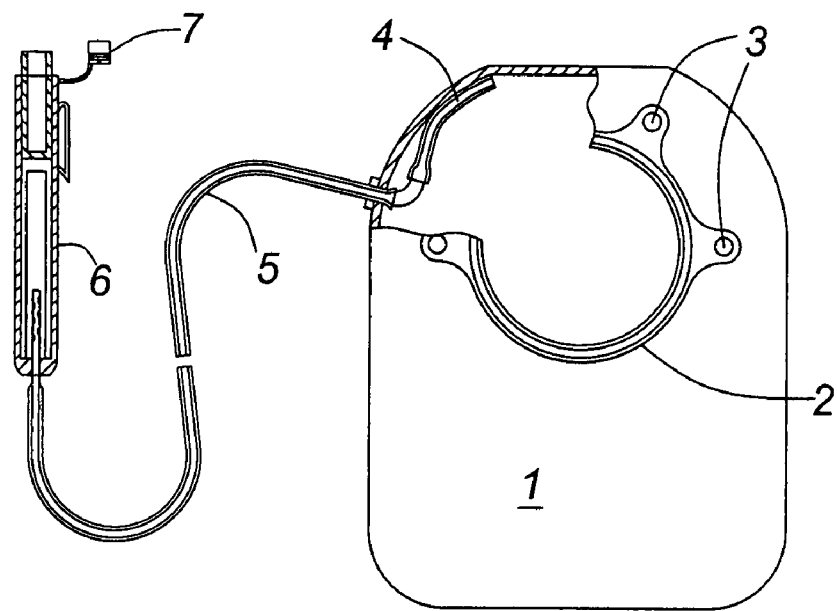
FIG. 1 is a part sectional rear elevational view of a colostomy bag according to the prior art.
Figure 2:
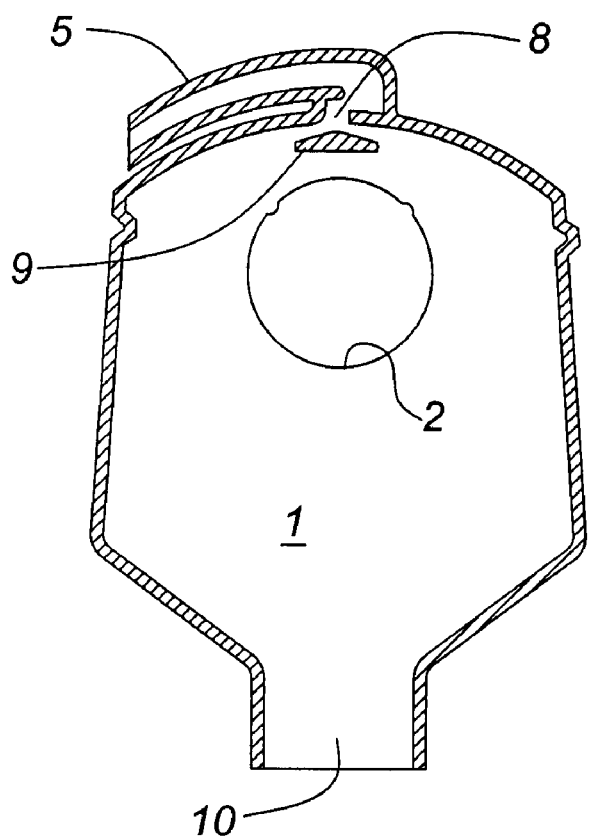
FIG. 2 is a part sectional rear elevational view of an alternative colostomy bag according to the prior art.

In FIG. 1 there is shown, in operative position, a typical colostomy bag 1, according to the prior art, including a stoma ring 2 for placement against the stoma in the patient's abdominal wall, belt attachment points 3, an internal vent tube 4 heat sealed adjacent an upper inner wall of the bag 1 and venting via external tube 5 to an external deodourizing filter 6, the exit of which is provided with a removable cap 7. The bag 1 is fabricated by heat sealing two planar flexible thermoplastic sheets together around the periphery of the bag. FIG. 2 shows, in operative position, a somewhat similar prior art bag 1 having a stoma ring 2, an external vent tube 5 at the top of the bag the vent opening 8 being protected by a small horizontal baffle 9 formed by heat sealing the opposing inner faces of the thermoplastic sheets from which the bag is formed in the area adjacent the vent 8. A drain 10 may be provided at the lower end of the bag to facilitate emptying thereof.

Figure 3:
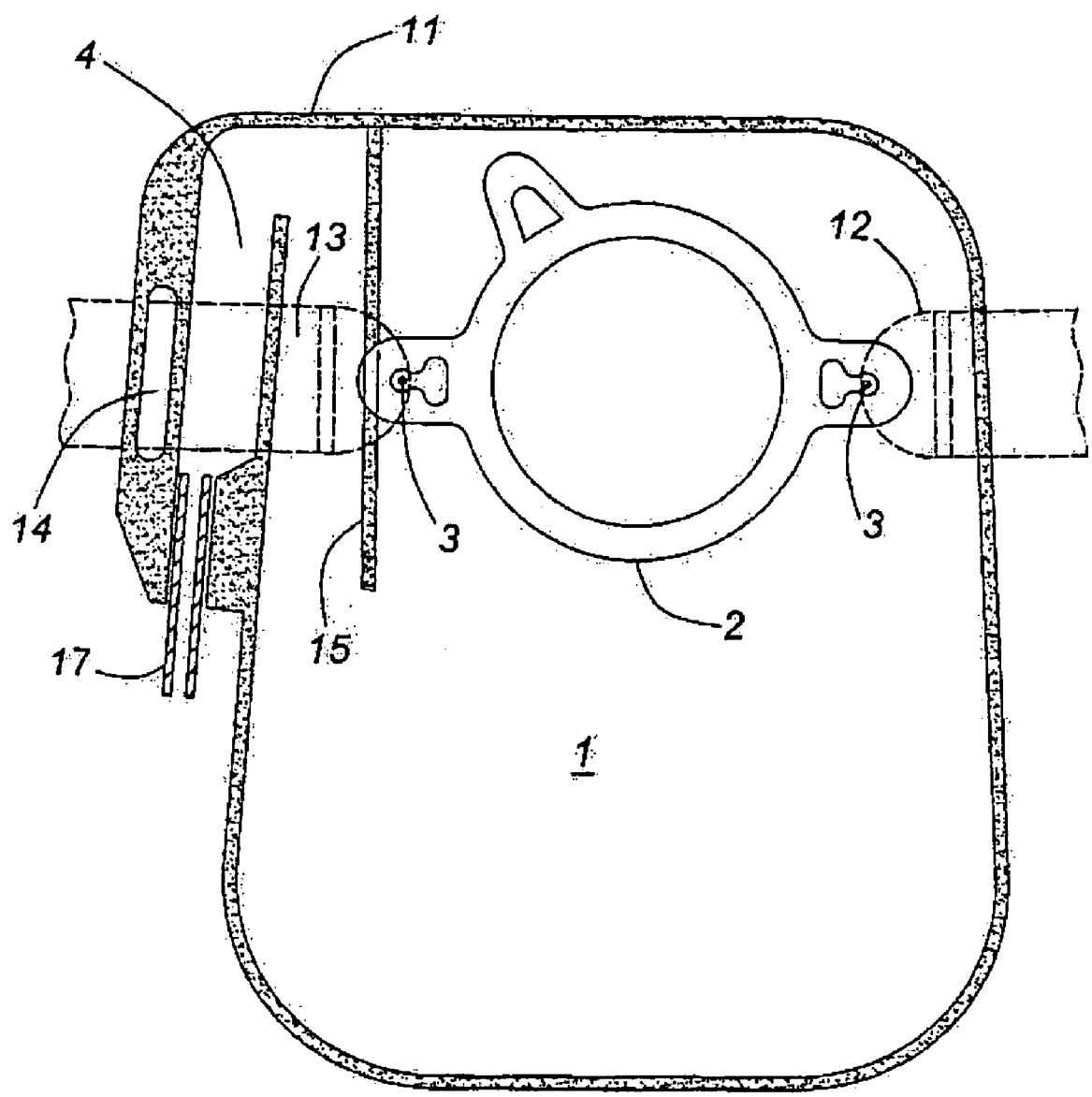
FIG. 3 is a part sectional rear elevational view of a colostomy bag according to one embodiment of the present invention.

In FIG. 3 there is shown a colostomy bag 1, according to the present invention, formed from two planar sheets of flexible thermoplastic material, such as polyethylene, heat sealed around the perimeter thereof, which is similarly provided with a stoma ring 2, belt attachment points 3, to receive and releasably secure respective ends 12, 13 of a body encircling belt, and a vent tube 4 heat sealed through the wall of the bag 1 adjacent an upper end 11 of the bag 1. Optionally, but not essentially, a belt loop 14 may be provided to facilitate accurate location of the bag relative to the patient's stoma. As the bag 1 is normally located adjacent the patient's waist, where his/her clothing is often relatively tight, it has been found that feces entering the bag via stoma ring 2 tends to be squeezed sideways before sinking, under gravity, to the bottom of the bag and that even the provision of a horizontal baffle 9 does not prevent feces from being squeezed into the vent 4 which quickly becomes plugged and ineffective, often within the space of a few hours. It has now been found, however, that the problem of vent plugging can be substantially eliminated by the provision of a vertical baffle 15 extending from the heat seal at the upper end 11 of bag 1 to a level slightly below the bottom of stoma ring 2. Baffle 15 is most easily formed by heat sealing the opposed inner faces of the thermoplastic sheets forming bag 1 together. Feces entering the bag 1 and squeezed sideways contact the baffle 15 and are diverted downwardly, under gravity, and directly away from vent 4 which remains clear usually for several days at least. Alternative methods of baffle formation will be apparent to those skilled in the art.

Figure 4:
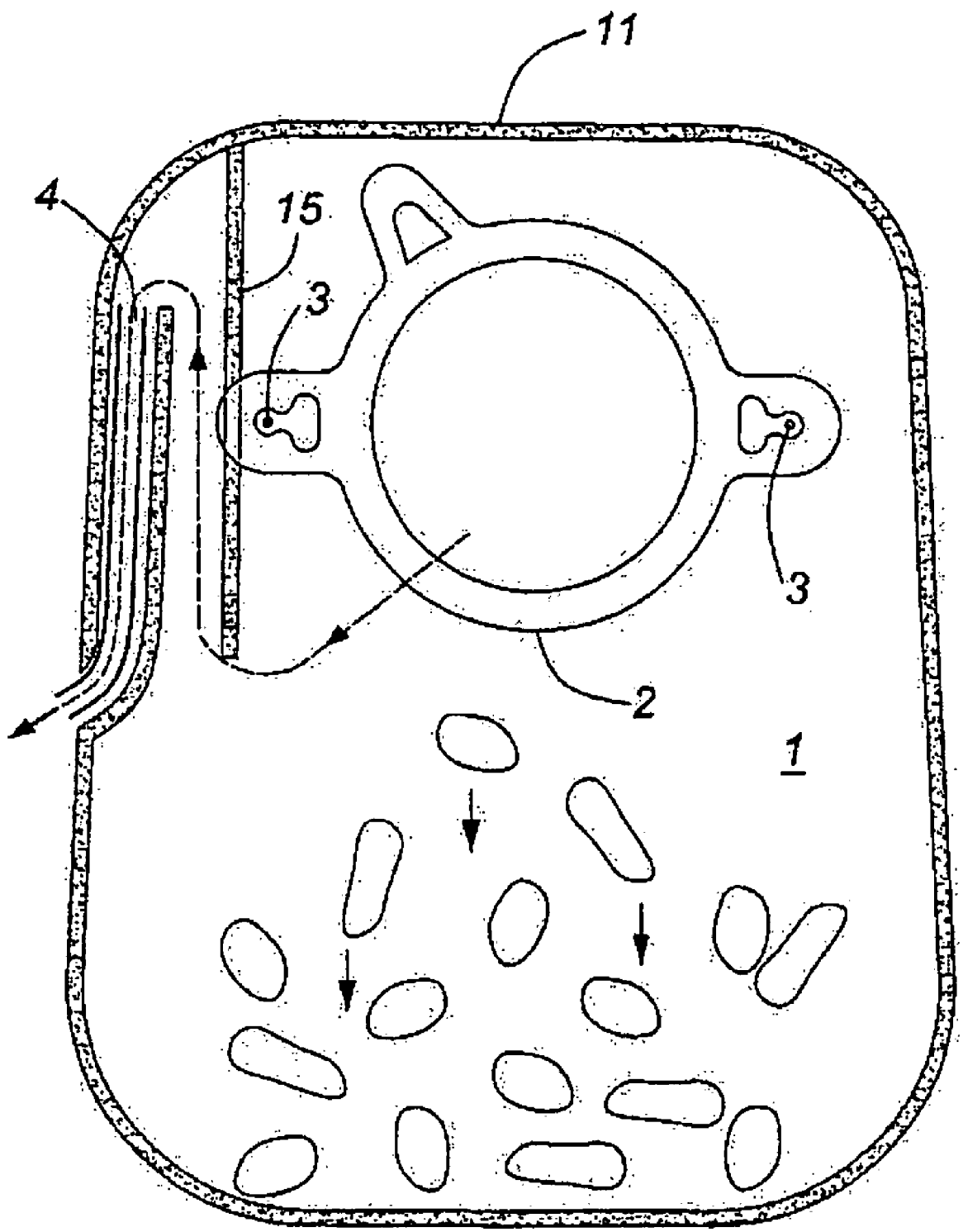
FIG. 4 is a part sectional rear elevational view of an alternative embodiment of a colostomy bag according to the present invention.
Figure 5:
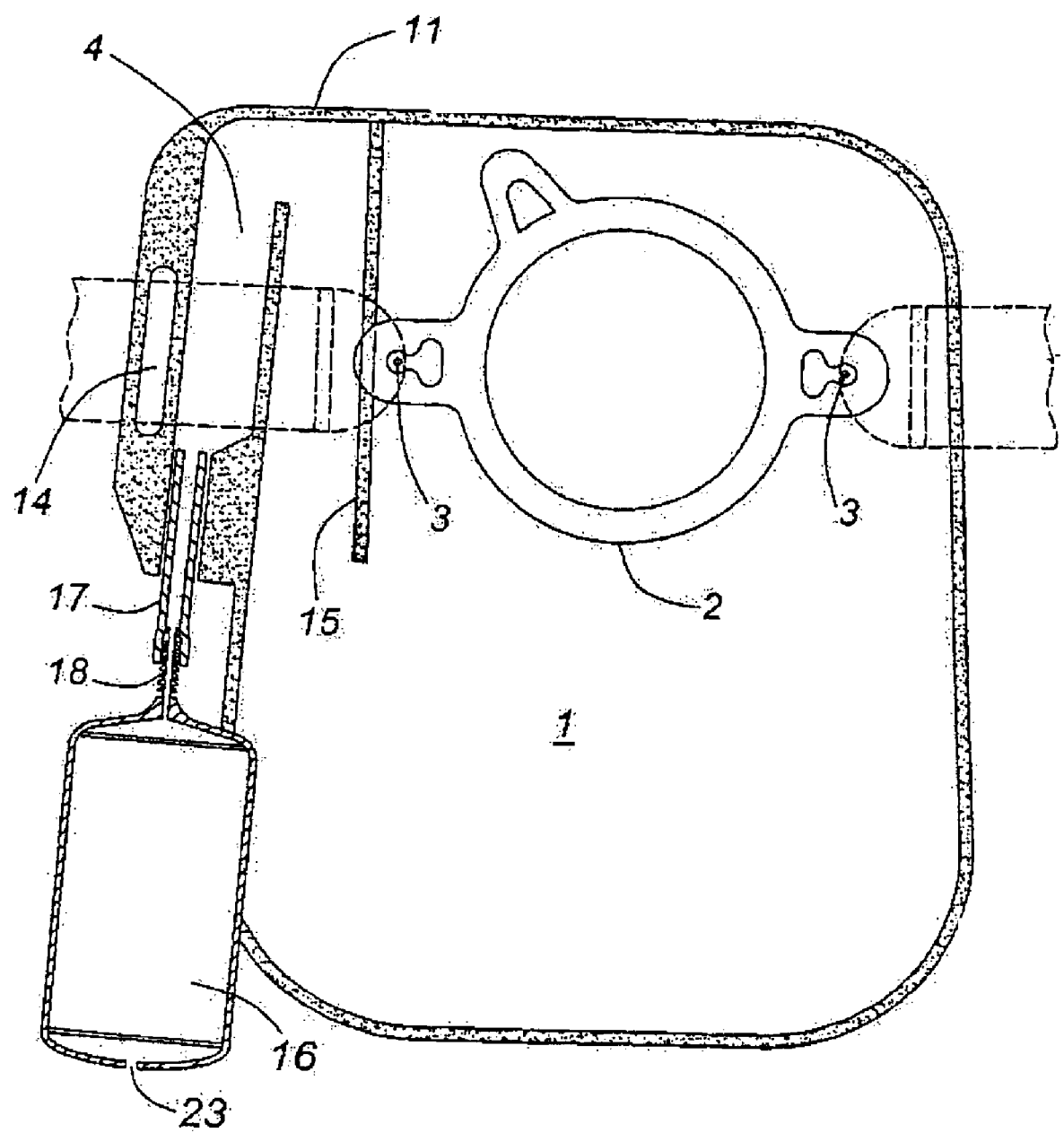
FIG. 5 is a part sectional rear elevational view of the colostomy bag of FIG. 3 with an external deodorizing filter attached.
Figure 6:
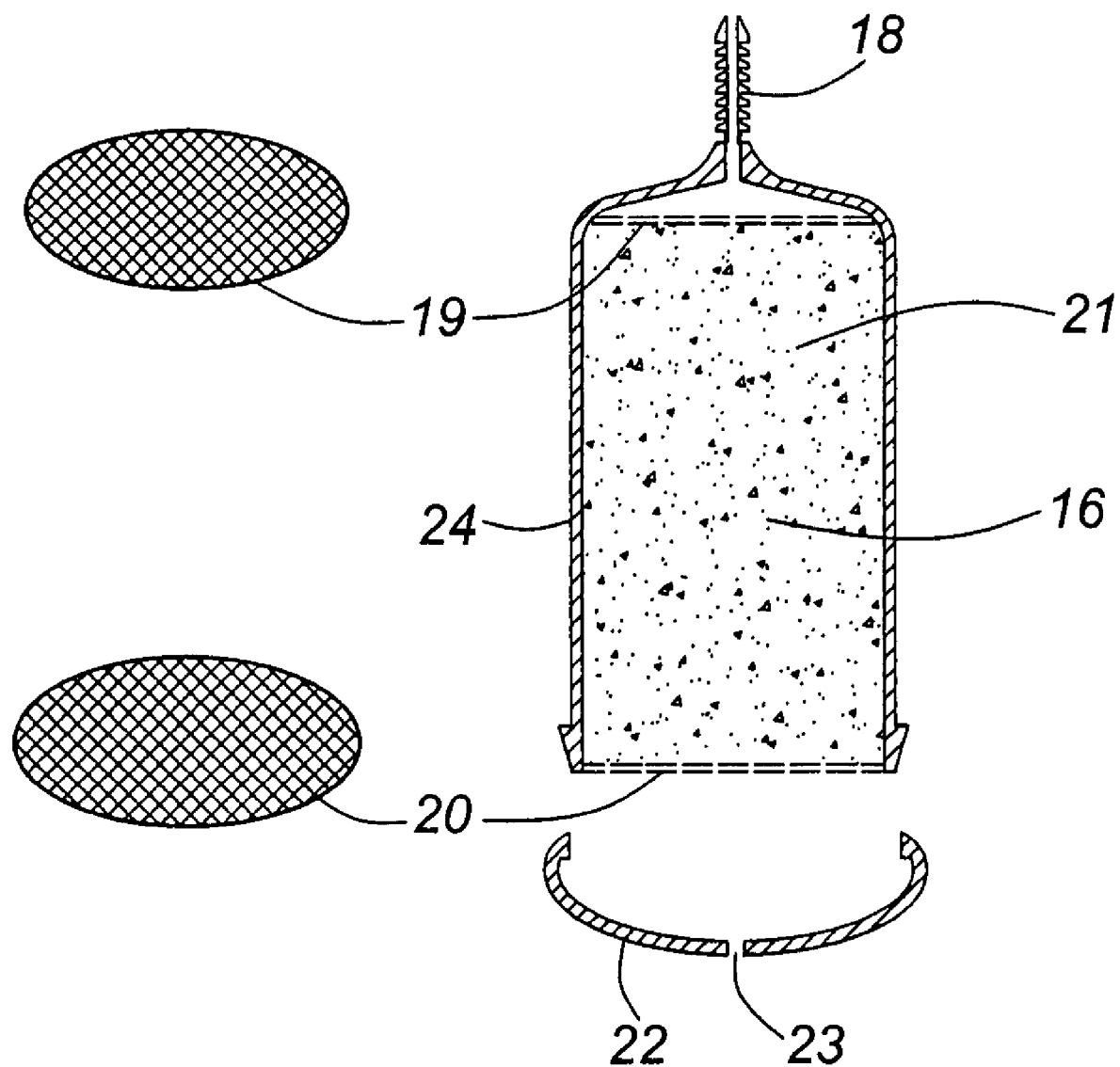
FIG. 6 is an exploded view of the filter shown in FIG. 5.

FIG. 4 shows a slightly modified embodiment of the invention of FIG. 3, which omits belt loop 14 and shows a slightly different attachment of vent tube 4. In operation the embodiments of FIGS. 3 and 4 function in the same way, with the vertical baffle 15 diverting feces away from vent 4. FIG. 5 illustrates one way of attaching an external deodorizing filter 16 to the outlet of the vent 4. A flexible tube 17 is heat sealed into vent 4 and tube 18, integral with filter 16, is releasably secured therein. As seen more clearly in FIG. 6, filter 16 includes an inlet tube 18 adapted to releasably engage tube 17, inlet and outlet screens 19, 20 to contain any conventional particulate deodorizing filter medium 21, such as activated charcoal, therebetween, and an outlet cap 22, provided with a restricted gas outlet 23 and designed for releasable engagement with sidewalls 24 of filter 16. Optionally, but not essentially, outlet 23 may be provided with a removable plug (not shown) if continuous release of gases is not required or desirable for aesthetic reasons.

I claim:

1. A colostomy bag formed by a pair of superimposed planar sheets of a flexible thermoplastic material heat sealed to each other around the marginal edges thereof, the colostomy bag having an upper marginal edge, first and second side edges and a lower marginal edge, said bag, when in operational position, including:
   (i) a stoma ring positioned adjacent the upper marginal edge of the bag above a horizontal midline of the bag so as to provide a feces and gas inlet means above the horizontal midline;
   (ii) a vent tube and gas outlet formed as an opening in the first or second side edge, the vent tube and gas outlet positioned above the horizontal midline; and
   (iii) a vertical baffle intermediate between said stoma ring and the vent tube and gas outlet, the vertical baffle extending vertically from and sealing against the upper marginal edge of the bag to a position below a lower edge of the stoma ring, so as to divert feces away from the vent tube and gas outlet and toward the lower marginal edge of the bag wherein the vertical baffle is formed by sealing a portion of the superimposed planar sheets of a flexible thermoplastic material together,
   (iv) wherein the vent tube extends the gas outlet upwardly towards the upper marginal edge of the bag so as to substantially overlap with the vertical baffle above the midline and to define a circuitous path above the midline between the stoma ring and gas outlet above the midline to provide separation of gas and feces during use.

2. A colostomy bag as claimed in claim 1 including a filtering and deodorizing system operatively connected to the gas outlet.

3. A colostomy bag as claimed in claim 2 wherein said filtering and deodorizing system comprises an external filter releasably connected to the gas outlet.

4. A colostomy bag as claimed in claim 2 wherein the filtering and deodorizing system includes a particulate deodorizing medium.

5. A colostomy bag as claimed in claim 1 wherein the stoma ring includes a belt attachment system.

* * * * *